United States Patent [19]
Mantelle et al.

[11] Patent Number: 5,725,876
[45] Date of Patent: Mar. 10, 1998

[54] COMPOSITIONS AND METHODS FOR USING LOW-SWELL CLAYS IN NICOTINE CONTAINING DERMAL COMPOSITIONS

[75] Inventors: Juan Mantelle; David Kanios, both of Miami, Fla.

[73] Assignee: Noven Pharmaceuticals Inc., Miami, Fla.

[21] Appl. No.: 649,512

[22] Filed: May 17, 1996

[51] Int. Cl.$^6$ .............................. A61L 15/20; A61L 15/26
[52] U.S. Cl. .............................. 424/449; 424/487
[58] Field of Search ..................... 424/449, 487

[56] References Cited

U.S. PATENT DOCUMENTS

| | | | |
|---|---|---|---|
| 5,077,104 | 12/1991 | Hunt et al. | 428/34.3 |
| 5,300,291 | 4/1994 | Sablotsky et al. | 424/78.18 |
| 5,474,783 | 12/1995 | Mikanda et al. | 424/448 |

FOREIGN PATENT DOCUMENTS

WO95/18603  7/1997  United Kingdom.

*Primary Examiner*—Peter F. Kulkosky
*Attorney, Agent, or Firm*—Foley & Lardner

[57] ABSTRACT

A dermal composition for transdermal administration of nicotine includes a blend of: one or more acrylic-based polymers in an amount of from about 10–90% w/w, nicotine in an amount of from about 3 to 15% w/w, and a cohesiveness increasing amount of one or more low-swell clays in an amount of from about 0.5 to 30% w/w. The low-swell clay has a swell of 3–23 mls as determined by the bentonite USP/NF swelling power test. Also disclosed is a method for producing a dermal composition and a method for increasing the cohesiveness of a nicotine containing dermal composition.

16 Claims, 3 Drawing Sheets

COMPOSITIONS AND METHODS FOR USING LOW-SWELL CLAYS IN NICOTINE CONTAINING DERMAL COMPOSITIONS

BACKGROUND OF THE INVENTION

1. Field of the Invention

The present invention relates to compositions and methods for dermal administration of nicotine. More specifically, the present invention relates to the use of low-swell clays in dermal compositions containing nicotine. The present invention also relates to a method for the dermal administration of nicotine.

2. Description of the Related Art

Dermal compositions of a drug within a polymer matrix for systemic or topical sustained released drug delivery are known in the art. One problem with drugs which are normally liquid at room temperature, such as nicotine, or drugs which have been solubilized with other liquid components, is the plasticizing effect that the liquid has on the polymer matrix in the dermal composition. Namely, the liquid can have an excessive plasticizing effect on the polymer, resulting in a composition that is "leggy or gummy." This renders the composition unsuitable for adhesion to the epidermis. Another difficulty with excessive liquidity in a dermal composition is the effect that the liquid has on the adhesiveness of the system.

The use of clays in dermal compositions is also generally known in the art. These clays are generally added as fillers as described in U.S. Pat. No. 4,421,737. Clays are also described as being used in dermal compositions for increasing the adhesiveness of these compositions as described in U.S. Pat. No. 5,300,291. The objective of using clay to increase other properties, such as cohesiveness, is also broadly described in U.S. Pat. No. 5,300,291 and in copending application Ser. No. 08/447,361. None of the related art, however, is able to describe what aspect of clay controls its effect on the wear and other properties a dermal composition, especially, in relation to cohesiveness or shear resistance.

SUMMARY OF THE INVENTION

One object of the present invention is to overcome the disadvantages of the known art described above. Another object of the present invention is to provide a dermal composition which uses a clay to improve wear properties of the composition based on the swell properties of the clay. Another object of the present invention is to provide a nicotine containing dermal composition which is simpler than those known in the art and has superior cohesiveness. Another object of the invention is to provide a method for administering nicotine to a mammal in need thereof. Yet another object of the present invention is to provide a method for producing the dermal composition according to the present invention. Still another object of the present invention is to control the wear properties of a dermal composition containing nicotine by selection of a clay based on its swell properties.

The foregoing and further objects are achieved according to one aspect of the present invention, which provides a method to control the cohesiveness of a dermal composition containing nicotine based on the swell properties of the clay. According to another aspect of the present invention there has been provided, a dermal composition comprising a blend of: one or more acrylic-based polymers; nicotine; and a cohesiveness increasing amount of one or more low-swell clays.

In another aspect of the present invention, there has been provided a method of administering a therapeutic amount of nicotine to a subject comprising the steps of: providing a composition according to the present invention; and contacting an area of a body with the composition for a sufficient time to administer a desired amount of the nicotine.

According to still a further aspect of the invention, there has been provided a method for producing a dermal composition which comprises: combining one or more polymers, nicotine, and one or more low-swell clays to form a dermal composition.

Further objects, features and advantages of the present invention will become apparent to those skilled in the art from consideration of the detailed description of preferred embodiments which follows.

DETAILED DESCRIPTION OF THE INVENTION INCLUDING PREFERRED EMBODIMENTS

Figure 1:
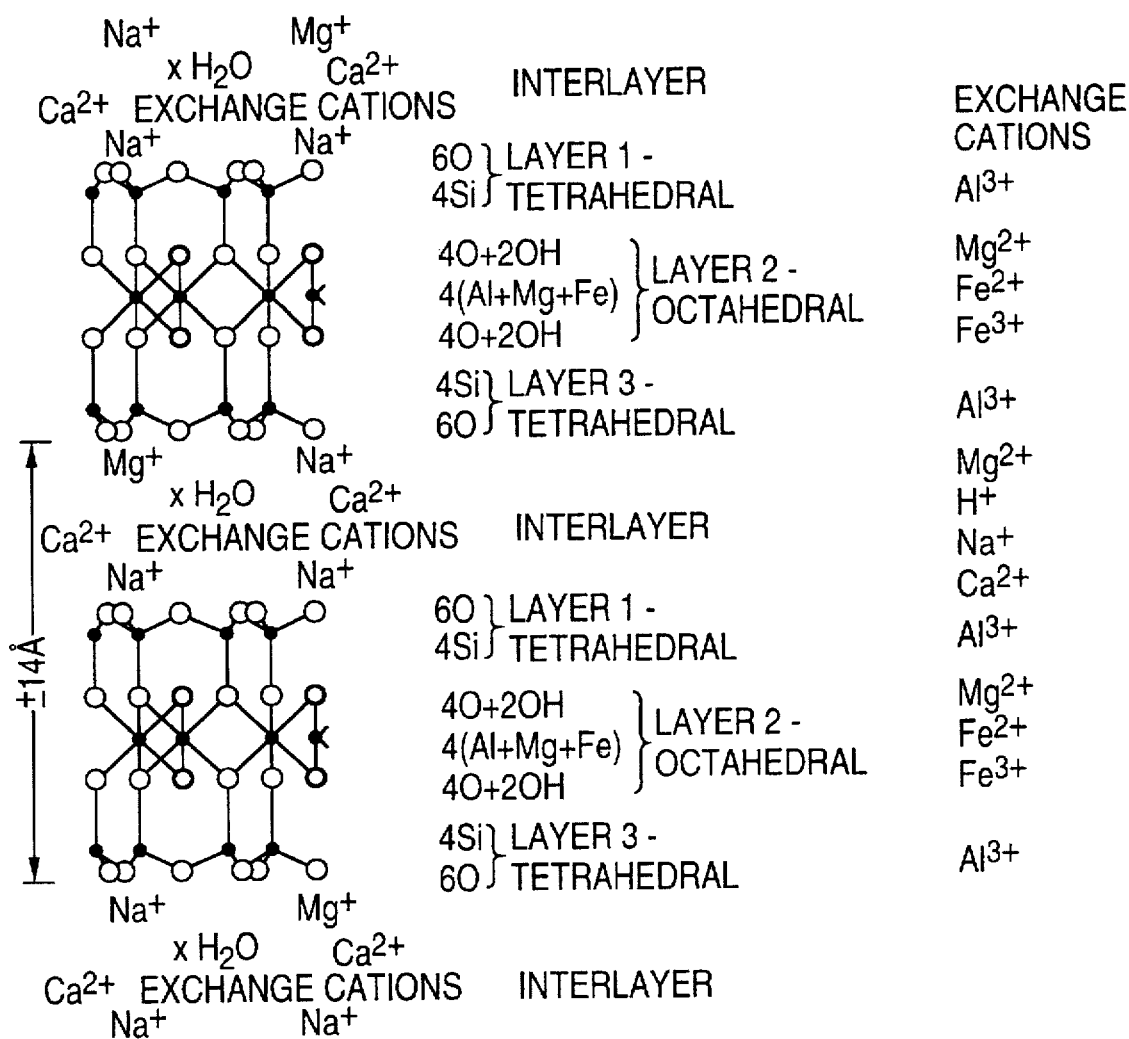
FIG. 1 depicts the structure and chemical composition of montmorillonite clay.
Figure 2:
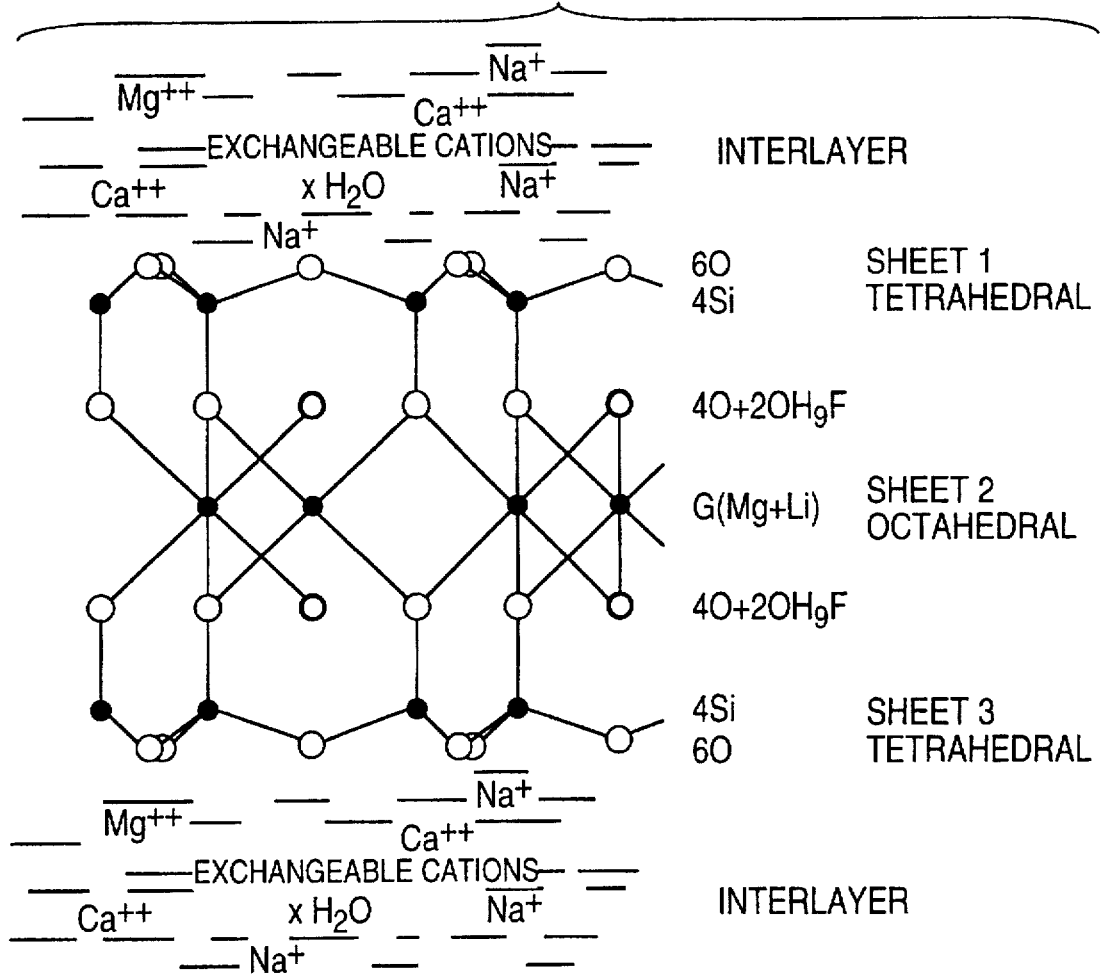
FIG. 2 depicts the structure and chemical composition of hectorite clay.

The term "dermal" is used here in its conventional sense as referring to an area, which can be in or on any part of the body, including but not limited to the epidermis, any other dermis, or any other body tissue. Dermal administration or application means the direct contact of the dermal composition with tissue, such as skin or membrane, oral or buccal mucosa. Such administration is also known as transdermal, percutaneous, mucosal or buccal administration. Typical administration is through the skin, mouth, nose, rectum, vagina or eye. Dermal administration also includes application to hardened tissue such as teeth and appendages of the skin such as nails and hair.

As used herein, a "dermal composition" is defined as a composition which contains nicotine therein. The dermal composition is applied to a dermal area, described above for dermal administration or application of the nicotine. The dermal composition includes a polymer matrix with the nicotine contained therein. As described below, in a preferred embodiment, the polymer matrix may be a pressure-sensitive adhesive for direct attachment to a user's skin. Alternatively, the polymer matrix may be non-adhesive with separate adhesion means for adhering the composition to the user's skin.

The invention relates to the unexpected discovery that the extent of swelling of a clay determines its effect on a dermal composition. As discussed above, the use of clays in dermal drug delivery systems is generally known in the art for use as either fillers or for increasing the amount of adhesiveness of the dermal polymer matrix of the drug delivery system. Until the present invention, however, it was not known that by selecting a clay based on its swell properties, its effect on the cohesiveness of a dermal composition, could be predictably determined.

The swelling of a clay describes a clay's ability to absorb liquid. Liquids as used herein, can be water and/or organic liquids. A high-swell clay can absorb more liquids than a corresponding low-swell clay. Swellability of the clay is determined using the Bentonite USP/NF swelling power test. This test is used as an industry standard with each company having its own test number, such as American Colloid Company Procedure No. 6514, which is expressly incorporated by reference in its entirety. The test comprises, adding two grams of clay in portions to 100 ml of water in a glass-stoppered graduated cylinder. Each portion of the clay is allowed to settle to the bottom of the cylinder before the next portion is added. The mass of clay is allowed to swell for 2 hours and the extent of swelling (i.e., the extent that the clay has risen on the graduated cylinder) is measured for the clay. Although this test is described using absorption of water, it is generally understood that a clay which absorbs water will also absorb other organic liquids albeit to varying degrees.

As used herein, a "low-swell" clay is defined as a clay which swells in a range of less than 24 mls using the above described test.

As used herein, a "high-swell" clay is defined as a clay which swells in a range of greater than or equal to 24 mls using the above described test.

The plasticizing effect of liquids, such as nicotine, in conventional dermal compositions, results in a marked decrease in shear resistance of the polymer matrix. This decreased shear resistance leads to legging or gumminess of the polymer to the point that it is no longer suitable for wear.

As used herein, "legs" are adhesive strings that can be seen when an adhesive flows. Legging is defined as the removal from the adhesive surface of small amounts of adhesive which in turn remain on the application surface upon removal of the product. On human skin, this legginess or gumminess shows up as a residue upon patch removal. "Legging" or "gumminess," is further defined when the shear resistance of the pressure-sensitive dermal system, is such that the dermal system will slip after application or leave a residue upon removal.

As used herein, "shear resistance" is defined as the force required to pull a pressure-sensitive tape for a standard flat surface in a direction parallel to the flat surface. In the present invention, the flat surface used to determine the shear resistance is a polished stainless steel plate. Shear resistance is an indicator of the cohesiveness of the dermal composition.

As used herein, the dermal composition of the present invention has "sufficient shear resistance" or "sufficient cohesiveness" if it does not slip after application or does not leave a significant residue after removal. The dermal composition according to the present invention generally has a shear resistance in the range of from about $\geq 15$ minutes with a 250 gram weight at 90° F. to $\leq 4$ hours with a 1000 gram weight at 90° F. Accordingly, if a dermal composition has a shear resistance less than this, it can be considered as having insufficient shear resistance or insufficient cohesiveness.

The present inventors surprisingly discovered that low-swell clays can be used to increase the shear resistance or cohesiveness of a dermal composition which has insufficient shear due to the plasticizing effect that a liquid drug, such as nicotine, has on the polymer system. This was completely unexpected in that it was generally assumed that if a clay was to be used, it should be one that has a high swell in order to absorb as much liquid as possible.

While not being bound by any theory, it is believed that when a low-swell clay is used in a dermal composition with insufficient shear resistance, the physical presence of the clay acts in a manner which prevents excess interaction of the liquid, such as nicotine, in the composition with itself and the polymer component of the composition. This restricted interaction prevents movement of the substituents (particularly the polymer) of the composition relative to each other with the end result being increased shear resistance of the dermal composition. In this type of system, there is relatively little absorption of the liquid in the system by the low-swell clay. Accordingly, substantially all of the liquid in the system is "free" i.e., not bound or trapped within the clay structure due to absorption by the clay.

It was surprisingly found that a high-swell clay could not necessarily be used in place of a low-swell clay, due to the excess absorption of the liquid, such as nicotine, in the system. Specifically, the high-swell clay would increase cohesiveness to an extent, but due to the absorptive effect of the high-swell clay, the composition would fail before enough cohesiveness increasing effect of the clay had been reached. This is due to the fact that the swelled clay loses its shear building ability by occupying a greater percentage of the composition surface area. Since the clay itself does not have adhesive properties, it effects a "dilution" of the adhesive properties by taking up the area previously occupied by the adhesive.

Clays which can be used according to the present invention include smectite clays. Smectites include montmorillonites, beidellite, nontronite, saponite, and hectorite. Particularly useful are montmorillonites and hectorites.

The absorbability of smectites is controlled by their chemical compositions and physical structure. All smectites varieties generally have the same basic crystal structure except for their metal cation content. The smectite structure is a two sheet structure with the first structure having its cations, mainly silicon, tetrahedrally coordinated. The other sheet structure has mono-, di- and tri-valent cations octahedrally coordinated. The sheets are bonded together by shared oxygen anions. The structure of the combined tetrahedral and octahedral sheet is extended in the z direction (i.e., in a direction perpendicular to the major surface of the sheet structure). Between these combined sheets are interlayers of cations which balance the negative charge on the sheets. The most common interlayer cations are those of sodium an calcium and to a lesser extent magnesium.

The smectites are also distinguished on the basis of whether they have a dioctrahedral and trioctahedral structure. This structure depends on the internal cation composition of the octahedral and tetrahedral sheets. Broadly stated, trioctahedral smectites have dominant amounts of magnesium ions in the octahedral layer. Various dioctrahedral and trioctahedral smectites are set forth in Table 1.

TABLE 1

| Dioctahderal Smectites | |
|---|---|
| Montmorillonite | $M^+ (Al_{2-y}(FeMg)_y)Si_4O_{10}(OH)_2 \cdot nH_2O$ |
| Beidellite | $M^+ Al_2(Si_{4-x}Al_x)O_{10}(OH)_2 \cdot nH_2O$ |
| Nontronite | $M^+Fe_2^{\ 3} + (Si_{4-x}Al_x)O_{10}(OH)_2 \cdot nH_2O$ |
| Trioctahedral Smectites | |
| Saponite | $M^+ (Mg_{3-y}(AlFe)_y Si_{4-x}Al_x)O_{10}(OH)_2 \cdot nH_2O$ |
| Hectorite | $M^+ (Mg_{3-y}Li_y)Si_4O_{10}(OH)_2 \cdot nH_2O$ |

It is the metal cation content of the interlayers and to a smaller extent the cation composition in the octahedral sheet that controls the swell properties of the clay. Specifically, a smectite with a higher concentration of sodium cations in the interlayer, as opposed to calcium cations will generally have a higher swell property.

A particularly useful smectite is montmorillonite. Montmorillonites are more commonly referred to as bentonites. A typical montmorillonite structure is shown in FIG. 1. As shown in FIG. 1 and Table 1, montmorillonite has a dioctrahedral structure and is generally classified as to whether it contains mainly Ca or Na cations in the interlayer. Bentonite which has Na cations in the interlayer is generally a high-swell clay, whereas Ca cations containing bentonites are low-swell. A comparison of homoionic bentonites in water is shown in Table 2. As Table 2 demonstrates, the swelling of sodium bentonite is four times greater than the calcium form.

Useful low swell bentonites are sold under the trade name (approximate swell in parenthesis) Bentolite L (5 ml), Gel-white L (23 ml) (both available from Southern Clay Products, Gonzales, Tex.), Carmargo White (8 ml), Magnabrite F (18 ml), Polargel NF (20 ml) and WDG-1 (23 ml) (available from American Colloid Company, Belle Fourche, S. Dak.).

High-swell bentonites are sold under the trade name Polargel HNF (27 ml), Polargel T (35 ml), and Magnabrite HV (52 ml) (all available from American Colloid Company). As used herein, a calcium bentonite is defined as bentonite with at least a 5:1 calcium to sodium ratio as the cations in the interlayers. As also used herein, sodium bentonite is defined as bentonite with at least a 1:1 sodium to calcium ratio as the cations in the interlayers.

TABLE 2

Behavior of Homoionic Montmorillonites in Water

|  | Sodium Montmorillonite | Calcium Montmorillonite |
|---|---|---|
| Free Swelling (2 g.) | 40 ml. | 10 ml. |
| Viscosity, 5% Suspension | 400 cps. | 20 cps. |
| Minimum Concentration for Gel Formation | 10% | 25% |

Typical chemical compositions of clays are set forth in Table 3.

$Mg^{++}$ in the octahedral layer substituted by $Li^+$. Hectorites due to their trioctahedral structure, generally have even a greater amount of swelling than bentonite clays. Hectorites are sold under the trade name Hectalite 200 (42 ml), Hectabrite DP (59 ml), and Hectabrite AW (64 ml). (All available from American Colloid Company.)

Smectite clays are further described in Technical Data Sheet IC-102, "Hectorite Deposits in the McDermitt Caldera of Nevada," American Colloid Company, Bell Fourche, S. Dak.; Technical Data Sheet IC-900, "Properties and Functions of Mineral Thickeners in Cosmetics and Toiletries," American Colloid Company; Technical Data Sheet IC-101, "Sodium Montmorillonite and Calcium Montmorillonite," American Colloid Company; Dell, D. J., Smectite Clays in Personal Care Products,"Cosmetics & Toiletries", Vol. 108, Pgs 79–85, May 1993; and Torok, A, "Useful Properties of Montmorillonites," Kaopolite, Inc., all of which are expressly incorporated by reference in their entireties.

The nicotine in the dermal composition can be present in a therapeutically effective amount. The term "therapeutically effective amount" as used herein with reference to the nicotine, is intended to mean the amount of nicotine sufficient to produce the desired effect when applied topically over the duration of intended use. The amounts necessary are known from the literature or may be determined by methods known in the art, and typically range from about 0.1 to 100 mg, and most preferably 0.5 to 30 mg per day, such as 11 or 22 mg per day, per human adult of about 75 kilograms body weight, depending upon whether the tissue, such as the skin or a mucous membrane is the site of action.

The therapeutic dosage and dosage unit amounts for the dermal route can be determined by standard tests known to those skilled in the art and an estimation of the dosage by the in vitro flux data using human cadaver skin. Alternatively, animal skin can be used to estimate the dosages as described in U.S. Pat. No. 4,751,087.

The dermal composition of the present invention further includes a mixture of one or more polymers blended in with the nicotine. The terms "blend" and "mixture" are used herein to mean that there is no, or substantially no, chemical reaction or cross-linking (other than simple H-bonding) between the different polymers in the polymer matrix.

TABLE 3

Chemical Analysis of Various Bentonites

| Sample # | $SiO_2$ % | $Al_2O_3$ % | $Fe_2O_3$ % | MnO % | MgO % | CaO % | $Na_2O$ % | $K_2O$ % | $TiO_2$ % | $P_2O_5$ % | LOI % | Total % | Ba PPM | Sr PPM | Y PPM | Sc PPM | Zr PPM |
|---|---|---|---|---|---|---|---|---|---|---|---|---|---|---|---|---|---|
| 389-42A | 66.66 | 11.09 | 1.16 | 0.02 | 2.53 | 1.46 | 2.36 | <0.01 | 0.09 | 0.01 | 13.36 | 96.15 | 641 | 188 | 15 | 2 | 102 |
| 389-42B | 67.75 | 11.17 | 1.25 | 0.02 | 3.34 | 1.44 | 2.32 | <0.01 | 0.09 | 0.02 | 12.53 | 99.27 | 572 | 178 | 13 | 2 | 97 |
| 389-42C | 46.21 | 2.09 | 0.93 | 0.07 | 20.69 | 5.32 | 3.17 | <0.01 | 0.19 | 0.02 | 20.81 | 98.83 | 834 | 338 | 10 | 10 | 84 |
| 389-42D | 67.33 | 12.56 | 1.3 | 0.01 | 2.72 | 1.64 | 2.62 | 0.14 | 0.12 | 0.04 | 12.27 | 100.74 | 119 | 177 | 9 | 4 | 91 |
| 389-42E | 59.67 | 16.72 | 0.99 | 0.02 | 3.09 | 1.48 | 2.69 | <0.01 | 0.19 | 0.12 | 15.26 | 99.9 | 619 | 171 | 26 | 3 | 131 |
| 389-102A | 69.6 | 8.46 | 0.02 | <0.01 | 2.17 | 1.66 | 0.16 | 0.12 | 0.2 | 0.05 | 17.1 | 99.54 | 67 | 123 | 14 | <2 | 167 |
| 389-102C | 61.5 | 10.4 | 0.06 | <0.01 | 4.39 | 2.52 | 0.38 | 0.07 | 0.27 | 0.03 | 19.6 | 99.42 | 287 | 148 | 6 | <2 | 379 |
| 389-102E | 71.3 | 11.7 | 0.07 | <0.01 | 2.01 | 1.38 | 1.15 | 0.12 | 0.14 | 0.3 | 12.8 | 100.97 | 277 | 278 | 9 | <2 | 173 |

389-42A Korthix H; Combustion Eng.
389-42B Polargel HNF - 26; American Colloid Co.
389-42C Hectolite 200; American Colloid Co.
389-42D Polargel NF; American Colloid Co.
389-42E Bentolite NF; Southern Clay
389-102A Bentolite L; Southern Clay
389-102C Carmargo White; American Colloid
389-102E WDG1; American Colloid Co.

As noted above, in addition to bentonite another type of smectite is hectorite. As described above, hectorite is a trioctahedral smectite which has a significant amount of As used herein, the term "one or more polymers" is defined to mean that one or a multiple number (e.g., 2, 3 or more) polymers can be used as the polymer matrix of the present invention. There is theoretically no limit to the number of individual polymers which may be used in the dermal composition of the present invention. However, as described in detail below, a preferred composition preferably includes only an acrylic-based polymer as a pressure-sensitive adhesive.

Selection of the particular polymer composition is governed in large part by the desired rate of delivery of the nicotine and the desired adhesive properties. Those skilled in the art can readily determine the rate of nicotine delivery from the dermal composition in order to select a suitable combination of polymers for a particular application. Combinations of polymers based on their differing solubility parameters can be used, such as those described in U.S. Pat. No. 5,474,783, which is incorporated by reference in its entirety. Various techniques can be used to determine the rate of delivery of the nicotine from the polymer matrix. Illustratively, the rate of delivery can be determined by measuring the transfer of the nicotine from one chamber to another through cadaver skin over time, and calculating, from the obtained data, the nicotine delivery or flux rate. Polymers which can be used according to the present invention vary broadly and generally depend on the delivery rate of the nicotine, and the type of device being fabricated (i.e., a matrix type wherein the polymer is both the reservoir and attachment means as opposed to a reservoir-type device).

In a preferred embodiment of the present invention, at least one of the one or more polymers is a pressure-sensitive adhesive, forming a pressure-sensitive adhesive polymer system. As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizer or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," said term being reserved for additives which differ other than in molecular weight from the polymers to which they are added.

The adhesive polymer system embodiment is preferably formulated so that it is a pressure-sensitive adhesive at or about room temperatures and has other desirable characteristics for adhesives used in the dermal drug delivery art. Such characteristics include good adherence to skin, ability to be peeled or otherwise removed without substantial trauma to the skin, retention of tack with aging, etc. In general, the adhesive polymer system should have a glass transition temperature ($T_g$), measured using a differential scanning calorimeter, of between about −70° C. and 0° C.

In a particularly preferred embodiment, the adhesive polymer system comprises an acrylic-based polymer. As used herein the term "acrylic-based" means any polyacrylate, polyacrylic and acrylic adhesive. The amount of acrylic-based polymer can range from about 10 to about 90 weight %, preferably about 25 to about 80 weight %, and more preferably about 40 to about 70 weight % based on the dry weight of the total dermal system with the amount of acrylic-based polymer being dependent on the amount of nicotine used.

The acrylic-based polymer can be any of the homopolymers, copolymers, terpolymers, and the like of various acrylic acids or esters. The acrylic-based polymers useful in practicing the invention are polymers of one or more monomers of acrylic acids and other copolymerizable monomers. The acrylic-based polymers also include copolymers of alkyl acrylates and/or methacrylates and/or copolymerizable secondary monomers or monomers with functional groups. By varying the amount of each type of monomer added, the cohesive properties of the resulting acrylic-based polymer can be changed as is known in the art. In general, the acrylic-based polymer is composed of at least 50% by weight of an acrylate or alkyl acrylate monomer, from 0 to 20% of a functional monomer copolymerizable with the acrylate, and from 0 to 40% of other monomers.

Further details and examples of acrylic adhesives which are suitable in the practice of the invention are described in Satas, "Acrylic Adhesives," *Handbook of Pressure-Sensitive Adhesive Technology*, 2nd ed., pp. 396–456 (D. Satas, ed.), Van Nostrand Reinhold, New York (1989), which is expressly incorporated by reference in its entirety.

Suitable acrylic adhesives are commercially available and include the acrylic-based polymer adhesives sold under the trademarks Duro-Tak 80-1194, 80-1196, 80-1197, 87-2287, 87-2516 and 87-2852 by National Starch and Chemical Corporation, Bridgewater, N.J. Other suitable acrylic adhesives are those sold under the trademarks Gelva-Multipolymer Solution GMS 737, 788, 1151 and 1430 (Monsanto; St. Louis, Mo.). Still other suitable acrylic adhesives are those sold under the trademark Morstik 703, 707, 705, 607, 709 and 605, all available from Morton International Corporation.

In another embodiment, the polymers selected are a blend of an acrylic-based and rubber-based polymer. As used herein, the term "rubber-based" refers to a viscoelastic material which contains at least one natural or synthetic elastomeric polymer. Suitable rubber-based polymers include silicone-based polymers, natural rubber, hydrocarbon polymers such as natural and synthetic polyisoprene, polybutylene and polyisobutylene, styrene/butadiene polymers, styrene-isoprene-styrene block copolymers, hydrocarbon polymers such as butyl rubber, halogen-containing polymers such as polyacrylo-nitrile, polytetrafluoroethylene, polyvinylchloride, polyvinylidene chloride, ethylene-vinyl acetate, polyvinyl alcohols, polyvinyl acetates, polyvinylpyrrolidones and polychloroprene and other copolymers thereof. In a preferred embodiment, the rubber-based polymer is a pressure-sensitive adhesive.

In still another embodiment, the polymer adhesive is a blend of the acrylic-based polymer described above and a silicone-based polymers (hereinafter referred to broadly as a polysiloxane). Selection of a proper blend is described in U.S. Pat. No. 5,474,783.

Suitable polysiloxanes include silicone pressure-sensitive adhesives which are based on two major components: a polymer, or elastomer, and a tackifying resin. The polysiloxane adhesive is usually prepared by cross-linking the elastomer, typically a high molecular weight polydiorganosiloxane, with the resin, to produce a three-dimensional siloxane structure, via a condensation reaction in an appropriate organic solvent. The ratio of resin to elastomer is the most important factor which can be adjusted in order to modify the physical properties of polysiloxane adhesives. Sobieski, et al., "Silicone Pressure Sensitive Adhesives," *Handbook of Pressure-Sensitive Adhesive Technology*, 2nd ed., pp. 508–517 (D. Satas, ed.), Van Nostrand Reinhold, New York (1989).

Further details and examples of silicone pressure-sensitive adhesives which are useful in the practice of this invention are described in the following U.S. Pat. Nos. 4,591,622; 4,584,355; 4,585,836; and 4,655,767, all expressly incorporated by reference in their entireties.

Suitable silicone pressure-sensitive adhesives are commercially available and include the silicone adhesives sold under the trademarks BIO-PSA X7-3027, X7-4203, Q7-4503, X7-4603, X7-4301, X7-4303, X7-4919, X7-2685, X7-4403, Q7-4501 and X7-3122 by Dow Corning Corporation, Medical Products, Midland, Mich.

If the dermal composition will be used in a moist environment, such as in buccal administration, the dermal composition preferably includes a bioadhesive. Particulars of bioadhesives can be found in copending application Ser. No. 08/447,361 and PCT US95/07229, both of which are incorporated herein by reference in their entireties.

The composition according to the present invention can be prepared, for example by mixing the one or more polymers, e.g. an acrylic-based pressure-sensitive adhesive, the nicotine, the low-swell clay in powder form, and optional ingredients in an appropriate volatile, lower molecular weight liquid. Preferably, the volatile, lower molecular weight liquid is an organic solvent supplied with the pressure sensitive adhesive, for example, the acrylic-based polymer. Typical liquids for solvent, as distinct from emulsion (typically aqueous) polymerization are volatile polar and non-polar organic liquids, such as lower molecular weight alkanols, such as isopropyl alcohol or ethanol, a benzene derivative such as xylene or toluene, lower molecular weight alkanes and cycloalkanes such as hexane, heptane and cyclohexane and alkanoic acid acetates such as ethyl acetate.

Preferably, the liquid mixture is cast at ambient temperature and pressure followed by evaporation of the volatile solvents, for example, by evaporation at slightly elevated temperatures, to form the dermal composition. The non-volatile or higher boiling solvents such as the polyols used in the composition remain therein. The dermal composition can then be cut into a defined geometric shape, if desired. The dermal composition can also be made by other conventional techniques.

Although it is believed that no appreciable amount of chemical reaction takes place between the components of the dermal composition, the present invention encompasses the end result of the blending and other manipulating of the components regardless of whether any such reaction occurs.

The nicotine, which is liquid at room temperature, requires no additional liquids, such as co-solvents, excipients and enhancers and preferably does not include any additional liquids. However, use of minor amounts of these liquids are not outside the scope of this embodiment. Minor amounts of additional liquids or "substantially no liquids" is defined as ≦10% w/w of additional liquids, preferably ≦5% w/w, and more preferably no additional liquid.

Additional liquids are defined herein as including enhancers, co-solvents, and excipients known in the art. A detailed listing of these liquids can be found in U.S. Pat. No. 5,474,783.

The acrylic-based polymer is also described as above. As noted above, the composition preferably includes only an acrylic-based polymer as the pressure-sensitive adhesive; however, small amounts of other polymers, pressure-sensitive adhesives or not, can be used and are not outside the scope of this embodiment. Small amounts of additional polymers or "substantially no additional polymers" is defined as ≦10% w/w of additional polymers, preferably ≦5% w/w and most preferably no additional polymers.

The low-swell clay used according to this embodiment, generally has a swell of 3–23 ml, preferably 5–18 ml, more preferably 5–12 ml. Particularly useful low-swell clays are Bentolite L and Carmargo White which have been described above.

In general, the dermal composition containing nicotine can comprise the following types and amounts of ingredients:

| Ingredient | % (w/w) in Final Composition | | |
|---|---|---|---|
| | Typical Range | Preferred Range | Optimum Range |
| nicotine | 3–15 | 5–12 | 7–10 |
| acrylic based polymer | 40–95 | 50–85 | 55–75 |
| low-swell clay | 0.5–30 | 8–25 | 15–22 |
| enhancer/ solvent | 0–10 | 0–5 | 0.0 |
| rubber based polymer | 0–15 | 0–7.5 | 0.0 |

The following examples further describe the instant invention, and are used for purposes of illustration only, and should not be considered as limiting in any way the invention being disclosed herein. In these examples, percentages refer to percentage by weight of ingredients.

EXAMPLES 1 AND 2 AND COMPARATIVE EXAMPLES 1 AND 2

A nicotine-polymer masterbatch was prepared by combining 89.66 g Gelva 788 acrylic polymer solution with 5.00 grams of nicotine. For each of the examples, a 15.78 g portion of the masterbatch was used in conjunction with the other indicated components to form a dermal composition with the components shown in Table 4 below representing the dry composition.

TABLE 4

| component (percent) | Example 1 | Example 2 | Comparative Example 1 | Comparative Example 2 |
|---|---|---|---|---|
| Nicotine | 10% | 10% | 10% | 10% |
| Polymer (Gelva 788) | 73.3% | 73.3% | 73.3% | 73.3% |
| Bentolite L | 16.7% | | | |
| Polargel HNF | | | 16.7% | |
| Hectabrite DP | | | | 16.7% |
| Carmargo White | | 16.7% | | |

After thorough mixing, the resulting mixture was coated onto a release liner and allowed to age for predetermined periods of time. After the predetermined period of time, the shear strength of the composition was then determined. Each sample was prepared by cutting strips having at least one side squared to an edge of 90° and a width of ¾", and a length of approximately 1¾".

The release liner was removed from each sample and the square-edged side pressed onto a standard 2"×5" stainless steel test panel with a ½" scored line, and aligned at the score line. A 4½ lb. machine automated roller was unidirectionally rolled over the portion of the sample attached to the steel test panel until the air bubbles were present.

A binder clip (BC-20, ¾", Officemate International Corp. or equivalent) from which to hang a 250 gram weight was then clipped on the opposite side of the sample. In order to evenly distribute the load weight, a piece of manila paper covers the entire width of the sample was pressed and stapled to this edge side before clipping on the binder clip.

Each entire test sample was mounted into the shear tester (Chemsultants International Shear Tester or equivalent) and a 250 gram weight was attached to each binder clip. The time (minutes) required for each sample to separate from the stainless steel test panel was recorded as shown below in Table 5.

TABLE 5

| Aging Time (Room Temperature) | Example 1 | Example 2 | Comparative Example 1 | Comparative Example 2 |
| --- | --- | --- | --- | --- |
| 1 day | 22.1 | 27.5 | 12.2 | 4.9 |
| 5 days | 23.0 | 31.4 | 13.8 | 6.6 |
| 8 days | 26.33 | 29.97 | 13.43 | 6.8 |
| 2 weeks | 22.9 | 29.9 | 14.5 | 7.5 |

Figure 3:
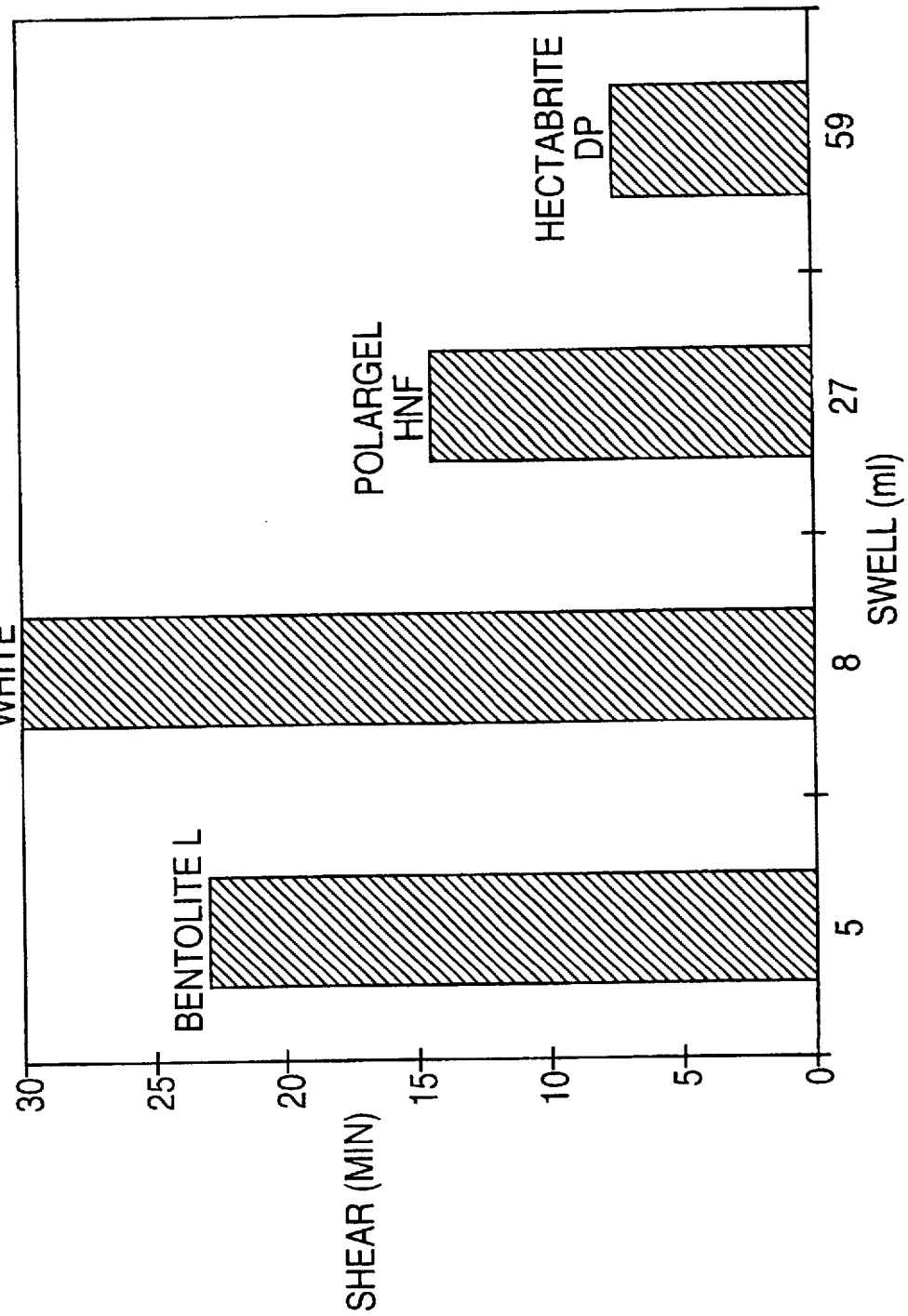
FIG. 3 is a bar graph of nicotine containing dermal composition with various high and low-swell clays.

The results for the shear resistance at two weeks were are shown in the bar graphs in FIG. 3. As FIG. 3 indicates, a lower swelling clay provides for increased shear resistance.

Other embodiments of the invention will be apparent to those skilled in the art from consideration of the specification and practice of the invention disclosed herein. It is intended that the specification be considered as exemplary only, with the true scope and spirit of the invention being indicated by the following claims.

What is claimed is:

1. A dermal composition comprising a blend of:
   one or more acrylic-based polymers in an amount of from about 10–90% w/w, nicotine in an amount of from about 3 to 15% w/w, and a cohesiveness increasing amount of one or more low-swell clays in an amount of from about 0.5 to 90% w/w, wherein the low-swell clay has a swell of 3–23 mls as determined by the bentonite USP/NF swelling power test.

2. A dermal composition as claimed in claim 1, wherein the composition is a pressure-sensitive adhesive and is capable of adhering to a user's skin.

3. A dermal composition as claimed in claim 2, wherein the composition is a matrix which is both a reservoir for the nicotine and an attachment means for attaching the composition to a user's dermis.

4. A dermal composition as claimed in claim 1, wherein the composition contains substantially no additional liquids.

5. A dermal composition as claimed in claim 1, wherein the composition contains substantially no additional polymers.

6. A dermal composition as claimed in claim 1, further comprising a backing layer and a release layer.

7. A dermal composition as claimed in claim 1, wherein the low-swell clay has a swell of 5–18 mls as determined by the bentonite USP/NF swelling power test.

8. A dermal composition as claimed in claim 7, wherein the low-swell clay has a swell of 5–12 mls.

9. A dermal composition as claimed in claim 1, wherein the low-swell clay is a calcium bentonite clay.

10. A dermal composition as claimed in claim 1, wherein the low-swell clay is present in an amount of from 8–25% w/w.

11. A dermal composition as claimed in claim 1, wherein the low-swell clay is present in an amount of from 15–22% w/w.

12. A dermal composition as claimed in claim 1, wherein the nicotine is present of from 7–10% w/w.

13. A method of administering a therapeutic amount of nicotine to a subject comprising the steps of:
   providing a composition as claimed in claim 1; and
   contacting an area of skin or mucous membrane with the composition for a sufficient time to administer the pharmaceutically active agent.

14. A composition as claimed in claim 1, made by a process comprising, blending one or more acrylic-based polymers; nicotine; and a cohesiveness increasing amount of one or more low-swell clays.

15. A method for producing a dermal composition according to claim 1 which comprises:
   combining one or more acrylic-based polymers, nicotine, and one or more low-swell clays form a dermal composition.

16. A method for increasing the cohesiveness of a nicotine containing dermal composition according to claim 1 which comprises:
   selecting a low-swell clay and
   combining the low-swell clay with one or more acrylic-based polymer and nicotine.

* * * * *